US008868205B2

(12) United States Patent
Ross et al.

(10) Patent No.: US 8,868,205 B2
(45) Date of Patent: Oct. 21, 2014

(54) SYSTEM AND METHOD FOR DETERMINING PHYSIOLOGICAL PARAMETERS BASED ON ELECTRICAL IMPEDANCE MEASUREMENTS

(75) Inventors: Alexander Seth Ross, Albany, NY (US); Jeffrey Michael Ashe, Gloversville, NY (US)

(73) Assignee: General Electric Company, Niskayuna, NY (US)

( * ) Notice: Subject to any disclaimer, the term of this patent is extended or adjusted under 35 U.S.C. 154(b) by 821 days.

(21) Appl. No.: 12/973,718

(22) Filed: Dec. 20, 2010

(65) Prior Publication Data

US 2012/0157866 A1    Jun. 21, 2012

(51) Int. Cl.
*A61B 5/053* (2006.01)
*A61B 5/0402* (2006.01)
*A61B 5/00* (2006.01)

(52) U.S. Cl.
CPC ............. *A61B 5/0535* (2013.01); *A61B 5/0402* (2013.01); *A61B 5/7214* (2013.01)
USPC ............ 607/115; 607/1; 607/2; 600/300; 600/301; 600/508; 600/509; 600/512; 600/513; 600/547

(58) Field of Classification Search
CPC .... A61B 5/0402; A61B 5/726; A61B 5/0006; A61B 5/0205; A61B 5/7257; A61B 5/0536; A61B 5/1128; A61B 5/7282; A61B 5/04; A61B 5/00; A61B 5/02; A61B 5/72; A61B 2018/00839; A61B 5/053; A61B 2018/00875; A61B 5/05; A61B 5/4836; A61B 5/7235; A61B 5/7253; A61N 1/3702; A61N 1/36521; A61N 1/36585; A61N 1/3956; G06Q 50/22; G06K 9/0053; G06T 11/006
USPC .......... 600/300–301, 508–509, 512–513, 547
See application file for complete search history.

(56) References Cited

U.S. PATENT DOCUMENTS

| 5,474,078 | A | * | 12/1995 | Hutson ........................ 600/512 |
|---|---|---|---|---|
| 5,713,367 | A | | 2/1998 | Arnold et al. |
| 6,512,949 | B1 | | 1/2003 | Combs et al. |
| 2005/0203431 | A1 | | 9/2005 | Brodnick et al. |
| 2007/0142733 | A1 | | 6/2007 | Hatlestad et al. |
| 2009/0182318 | A1 | | 7/2009 | Abboud et al. |
| 2010/0094376 | A1 | | 4/2010 | Penner |

FOREIGN PATENT DOCUMENTS

| EP | 2228009 A1 | 9/2010 |
|---|---|---|
| WO | 9410905 A1 | 5/1994 |
| WO | 2007121756 A2 | 11/2007 |

OTHER PUBLICATIONS

Search Report and Written Opinion from corresponding EP Application No. 11193211.7-2319 dated Jun. 25, 2012.

(Continued)

*Primary Examiner* — Deborah Malamud
(74) *Attorney, Agent, or Firm* — Melissa K. Dobson

(57) ABSTRACT

A system and method for determining physiological parameters based on electrical impedance measurements is provided. One method includes obtaining electrical measurement signals acquired from a plurality of transducers coupled to a surface of an object and constructing a system matrix to define one or more relationships between the impedance measurement signals. The method also includes decomposing the system matrix to separate the electrical measurement signals.

17 Claims, 6 Drawing Sheets

(56) References Cited

OTHER PUBLICATIONS

Ansari et al, "Extraction of Respiratory Rate from Impedance Signal Measured on Arm: A Portable Respiratory Rate Measurement Device", IEEE International Conference on Bioinformatics and Biomedicine, 2009, pp. 197-202, Nov. 1-4, 2009.

Search Report and Written Opinion from corresponding EP Application No. 11193211.7-2319 dated Oct. 1, 2012.

* cited by examiner

SYSTEM AND METHOD FOR DETERMINING PHYSIOLOGICAL PARAMETERS BASED ON ELECTRICAL IMPEDANCE MEASUREMENTS

BACKGROUND

This subject matter disclosed herein relates generally to physiological monitoring systems, and more particularly to systems and methods to extract physiological parameters from electrical impedance measurements.

Electrical Impedance Spectroscopy (EIS) measurements are used to classify and quantify the complex electrical properties of materials, such as those that comprise a region of a human body. These electrical properties are determined by applying an electrical current or voltage, and measuring a response voltage or response current on one or more electrodes at a surface of the material under test. The applied excitation and measured response are processed to generate an estimate of complex electrical impedance. This process may be done using a single excitation, or this process may be repeated using two or more excitations to produce a measurement of a complex electrical impedance distribution that varies with the applied excitation. Electrical impedance measurements obtained by EIS systems can be used for monitoring human physiological parameters. The measurements may be obtained by applying very small electrical currents or voltages, using for example skin-contacting electrodes, and measuring the resulting voltages on the same or on different skin-contacting electrodes.

The obtained electrical impedance signals are a measure of several parameters, including the geometry (e.g., length, area and/or volume) between and among the electrodes and the complex electrical conductivity in the tissues between and beneath the electrodes (e.g. organs, muscle, fat and/or skin). Because the measured impedance is sensitive to variations in geometry, patient motion and other extraneous signal and noise sources can result in undesirable effects that corrupt (e.g., interfere with) underlying signals of interest, resulting in inaccurate measurements. The signals of interest may include, for example, respiration rate, cardiac pulsatility, and other anatomical and physiological phenomenon.

Known systems for monitoring respiration activity by impedance measurement use a single impedance measurement between two electrodes. The underlying source of interest is the airflow into and out of the lungs and the interfering sources include heart motion, patient movement, and other unrelated physiological motion. These interfering sources are inseparable with temporal or spectral techniques using a single impedance measurement between two electrodes.

Algorithms are also known to switch between different pairs of electrodes to avoid interference sources and improve signal visibility. For example, one method includes switching between a chest electrode that captures breathing motion due to dominant chest muscles and an abdomen electrode that captures motion due to dominant diaphragm muscles in abdomen-breathers. This method suffers from inseparability of desired and interfering sources.

Other known algorithms use information from a plurality of electrodes and employ electrical impedance tomography techniques to generate a reconstruction of the conductivity distribution of the interrogated area or volume. These systems can generate an image of the lungs filling or emptying of air, but require a multiplicity of electrodes, typically 16 or more, and a significant computing system for forward modeling and/or data and image reconstruction.

Non-electrical methods are also known for continuously measuring the ventilation rate of a patient. These methods may be performed by measuring airflow through the airway by intubation, using a mask or by a sensor in the nose or mouth of the patient. These continuous measurement methods are uncomfortable for the patient and accordingly not widely used. Other, less-intrusive methods may be performed using methods such as motion sensors, accelerometers, pressure sensors, microphones, acoustic sensors, and/or plethysmographic bands. These less-intrusive methods are prone to interference and motion artifact that reduces their sensitivity to measuring the physiological parameters of interest and inhibits their widespread use.

BRIEF DESCRIPTION

In accordance with an embodiment, a method for separating electrical measurement signals is provided. The method includes obtaining electrical measurement signals acquired from a plurality of transducers coupled to a surface of an object and constructing a system matrix to define one or more relationships between the electrical measurement signals. The method also includes decomposing the system matrix to separate the electrical measurement signals created from different physiological and non-physiological sources.

In accordance with another embodiment, a method for monitoring ventilation is provided. The method includes positioning a plurality of transducers on a surface of a body and obtaining electrical measurement signals from the plurality of transducers. The method also includes using a system matrix based process to separate the electrical impedance signals into ventilation measurement signals, ambulatory motion measurement signals, and other measurement signals not of interest to the ventilation analysis.

In accordance with yet another embodiment, an impedance measurement system is provided that includes a plurality of transducers configured for positioning on a surface of an object, wherein the plurality of transducers corresponds to a plurality of channels. The impedance measurement system also includes at least one excitation driver electrically coupled to the plurality of channels and configured to generate electrical excitations (e.g., currents or voltages) at the plurality of transducers and at least one response detector configured to measure a response at each of the plurality of transducers to define impedance measurement signals. The impedance measurement system further includes a processor having a physiological parameter extraction module configured to construct a system matrix to define one or more relationships between the impedance measurement signals and decompose the system matrix to separate the impedance measurement signals.

BRIEF DESCRIPTION OF THE DRAWINGS

The presently disclosed subject matter will be better understood from reading the following description of non-limiting embodiments, with reference to the attached drawings, wherein below.

DETAILED DESCRIPTION

Figure 1:
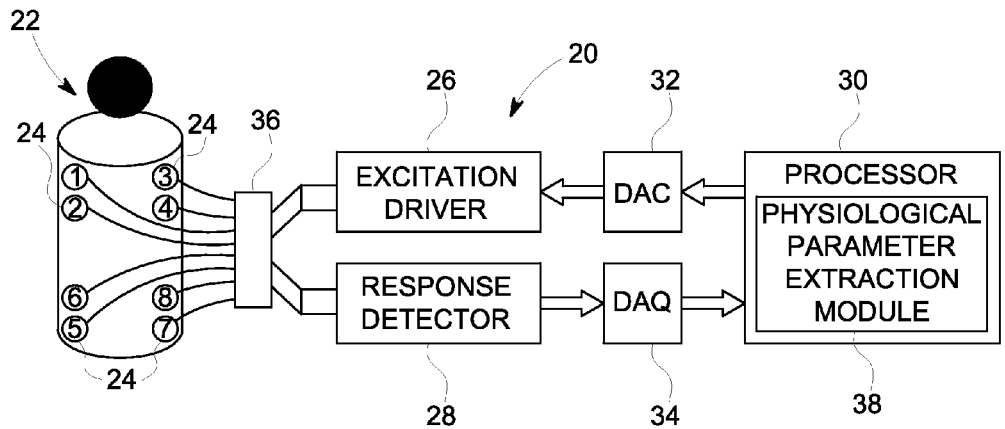
FIG. 1 is a simplified schematic block diagram illustrating an impedance measurement system formed in accordance with one embodiment.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, circuits or memories) may be implemented in a single piece of hardware or multiple pieces of hardware. It should be understood that the various embodiments are not limited to the arrangements and instrumentalities shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a system and method for separating or distinguishing electrical measurements of interest, such as desired physiological signals of interest, from electrical measurements that are not of interest, such as electrical impedance signals of physiological or non-physiological signals and noise sources that are not of interest. For example, in some embodiments, electrical impedance signals due to desired physiological activities (e.g., breathing) are separated from electrical impedance signals due to undesired physiological activities (e.g., heart or ambulatory motion) and from undesired non-physiological signals (e.g., noise) to perform real-time continuous monitoring of physiological activities. At least one technical effect is real-time continuous monitoring of physiological activities that may be performed using low complexity electronics and signal processing. For example, a patient monitor may be provided in accordance with various embodiments to measure electrical impedance to determine the respiration or breathing rate in comatose, sedated or sleeping patients, as well as in conscious patients exhibiting motion.

It should be noted that although various embodiments may be described in connection with an Electrical Impedance Spectroscopy (EIS) system or an Electrical Impedance Tomography (EIT) system having particular components, the various embodiments may be implemented in connection with any system that is capable of measuring electrical impedance of an object (e.g., a portion of a patient). Additionally, although the various embodiments may be described in connection with separating signals to identify ventilation rate separate from patient motion, other physiological and non-physiological signals or activities may be separated.

One embodiment of an impedance measurement system 20 is illustrated in FIG. 1, which may be a transducer-based system, for example, an electrode-based system, such as a patient monitor that may form part of an electrocardiography (ECG) monitoring device or an impedance cardiography module. However, the impedance measurement system 20 may also be an EIS/EIT system or other separate unit. The impedance measurement system 20 may be used to obtain electrical impedance measurements of an object 22 (e.g., a patient), which are used to separate physiological activities of interest from undesired physiological activities and non-physiological signals. For example, electrical impedance measurements obtained may be used in at least one embodiment to separate ventilation rate from patient motion.

In the illustrated embodiment, the impedance measurement system 20 includes a plurality of transducers 24, which in one embodiment is a plurality of electrodes, positioned at or proximate a surface of the object 22, which in a healthcare application (e.g., patient monitoring) may include attaching the plurality of the transducers 24 to the skin of a patient or subject. It should be noted that although eight transducers 24 are illustrated, more or fewer transducers 24 may be used. It should be noted that other types of transducers may be used to generate different types of excitations, for example, in addition to current, other sources of excitation include voltage, magnetic fields or radio-frequency waves, among others. Thus, the transducers also may be surface-contacting electrodes, standoff electrodes, antennas, and coils, among others.

The transducers 24 may be positioned at a surface of the object 22 in different arrangements and may be driven in different configurations. For example, the transducers 24 may electrodes and positioned at a surface of the object 22 using one of a plurality of standard ECG locations (e.g., Lead I, Lead II or Lead III ECG configurations). However, in other embodiments, different positioning of the transducers 24 in non-standard ECG locations may be provided (e.g., sub-axillary configurations). For example, the transducers 24 may be positioned to provide different views of trajectories/angles through the lungs and/or torso to provide increased sensitivity to breathing and decreased sensitivity to ambulatory motion. Additionally, combinations of the different positioning arrangements may be used such as having current driven transducers 24 in a Lead II configuration (right arm to left leg) and voltage measuring transducers 24 in a Lead I configuration (right arm to left arm), or vice versa. As other non-limiting examples of modification or variations, a configuration similar to the Lead II configuration may be provided, but with the right arm transducers 24 placed on the back of the shoulder (Lead II Back configuration) or with the current driven transducers 24 positioned in sub-axillary locations with voltage measurement transducers 24 on the front of the chest and center of the back.

Additionally, in various embodiments, the current driving one or more of the transducers 24 may be at the same carrier frequency, but with different phase (e.g., 0 degrees, 90 degrees, 180 degrees and 270 degrees). It should be noted that some of the transducers 24 may have no current applied thereto, but are used only for voltage measurements. Various exemplary embodiments of the settings (e.g., current driven and voltage measured) for the transducers 24 in different configurations is illustrated in Table 1 below:

TABLE 1

| Electrode Setting | | | | | | | | |
|---|---|---|---|---|---|---|---|---|
| 1 | 2 | 3 | 4 | 5 | 6 | 7 | 8 | Electrode Configuration |
| 0 | Vm | 180 | Vm | Vm | Vm | Vm | Vm | Conventional ECG Lead I |
| 0 | Vm | Vm | Vm | Vm | Vm | 180 | Vm | Conventional ECG Lead II |
| Vm | Vm | 0 | Vm | Vm | Vm | 180 | Vm | Conventional ECG Lead III |
| 0 | Vm | 180 | Vm | 0 | Vm | 180 | Vm | Right-to-Left |
| 0 | Vm | 0 | Vm | 180 | Vm | 180 | Vm | Top-to-Bottom |
| 0 | Vm | 180 | Vm | 180 | Vm | 0 | Vm | Diagonal |
| 0 | Vm | 90 | Vm | 180 | Vm | 270 | Vm | Rotating | wherein the symbols in Table 1 represent the following exemplary values:

| Symbol | Current | Phase |
|---|---|---|
| Vm | No Current - Voltage Measurement Only | |
| 0 | 60 uA | 0 deg |
| 90 | 60 uA | 90 deg |
| 180 | 60 uA | 180 deg |
| 270 | 60 uA | 270 deg |

It should be noted that the frequency for the applied currents illustrated above is 10 kHz, however as should be appreciated, other frequencies may be used. It also should be noted that one or more of the transducers 24 may be a ground reference or a reference for current return and noise cancellation purposes.

Referring again to FIG. 1, the impedance measurement system 20 also includes an excitation driver 26 and a response detector 28 that are coupled to the transducers 24, and which are each connected to a processor 30 (e.g., a computing device). In one embodiment, the excitation driver 26 and the response detector 28 are physically separate devices. In other embodiments, the excitation driver 26 and the response detector 28 are physically integrated as one element. The processor 30 sends instructions to the excitation driver 26 through a digital to analog converter (DAC) element 32 and receives data from the response detector 28 through a data-acquisition (DAQ) element 34. It should be noted that one or more excitation drivers 26 may be provided, such that one is provided per transducer 24, for a subset of transducers 24 or for all transducers 24.

In various embodiments, a four-wire measurement configuration is provided that uses the different pairs of transducers 24 for excitation from the excitation driver 26 and measurement by the response detector 28. The connection also may optionally be provided via an interface 36. Additionally, variations and modifications may be provided, such as using a two-wire configuration wherein the same pair of transducers 24 for excitation from the excitation driver 26 are used for measurement by the response detector 28.

The transducers 24 may be formed from any suitable conductive material used to establish a desired excitation. For example, the transducers 24 may be formed from one or more metals such as copper, gold, platinum, steel, silver, and alloys thereof. Other exemplary materials for forming the transducers 24 include non-metals that are electrically conductive, such as a silicon based materials used in combination with micro-circuits. In one embodiment, where the object 22 is a human body region, the transducers 24 are formed from silver-silver chloride. Additionally, the transducers 24 may be formed in different shapes and/or sizes, for example, as rod-shaped, flat plate-shaped, or needle-shaped structures. It should be noted that in some embodiments, the transducers 24 are insulated from one another. In other embodiments, the transducers 24 can be positioned in direct ohmic contact with the object 22 or capacitively coupled to the object 22.

In some embodiments, the transducers 24 are standard ECG electrodes having a surface area of about 1 square centimeter (sq. cm). However, different sized and shaped electrodes may be used, such as larger electrodes having a surface area of about or at least 70 sq. cm., where an increase in surface area may provide an increase in signal-to-noise ratio. However, the physiological parameter extraction of the various embodiments may be implemented in connection with any suitable size, shape or type of transducer 24.

In operation, the transducers 24 may be used to deliver electrical current continuously or optionally modulated such that excitations may be applied across a temporal frequency range (e.g., 1 kHz to 1 MHz) to the surface of the object 22 to generate an electromagnetic (EM) field within the object 22. The resulting surface potentials, namely the voltages (real, imaginary or complex) on the transducers 24 are measured to determine an electrical impedance (e.g. electrical conductivity or permittivity distribution), which is used to separate or distinguish different physiological parameters.

Thus, in various embodiments, the excitation driver 26 applies an excitation current to one or more of the transducers 24 with a voltage response measured by one or more the transducers 24. A physiological parameter extraction module 38, which may be implemented, for example, as software within the processor 30, then uses one or more system matrices of one or more relationships of different responses including but not limited to impedance signals or impedance measurements to distinguish different physiological parameters, which correspond in some embodiments to breathing and ambulatory motion.

Figure 2:
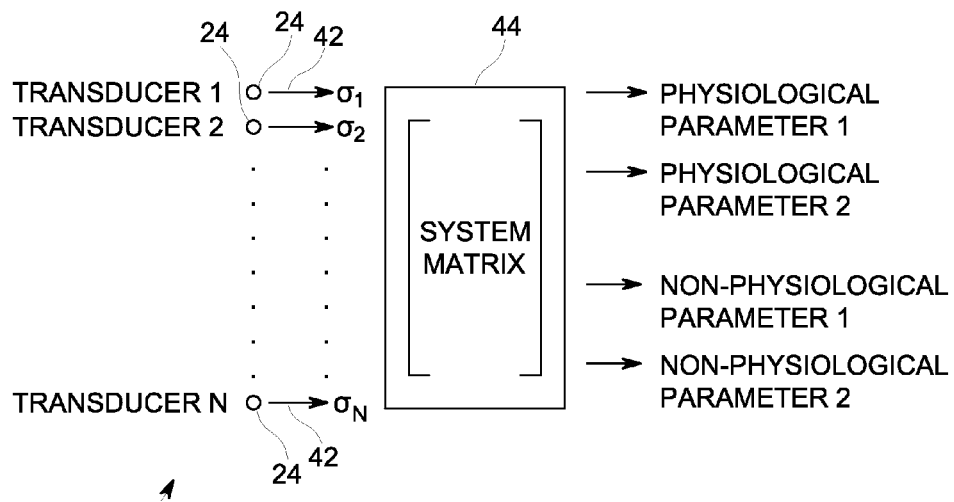
FIG. 2 is a simplified block diagram illustrating a physiological parameter extraction process performed in accordance with various embodiments.

Various embodiments and methods to separate or distinguish impedance signals will now be described in more detail. In particular a physiological extraction process 40 is illustrated in FIG. 2 wherein multiple electrical measurements (for example electrical impedance measurements illustrated as measurement signals 42 ($\sigma_1, \sigma_2, \ldots \sigma_N$)) are obtained from the plurality of transducers 24. It should be noted that although the measurement signals are illustrated as electrical conductivity measurements of the object 22, different measurements, such as different voltage, current, magnetic field, radiofrequency (RF) wave, or electrical impedance measurements may be made, for example, electrical permittivity measurements.

In various embodiments, the relationship of impedance changes among the transducers 24 is quantified into a system matrix 44. The one or more relationships among the set of signals is unique or at least descriptive/indicative of the underlying source, such as the source of body deformation caused by airflow into and out of the lungs. Thereafter, the system matrix 44 is separated using one of more techniques or methods to identify one or more underlying sources of interest. For example, as illustrated in FIG. 2, one or more physiological parameters may correspond to patient breathing, heart motion, ambulatory motion, or other patient motion and one or more non-physiological parameters may correspond to noise.

Thus, in various embodiments, a system matrix of relationships between impedance signals is used. The relationships may be, for example, voltages, voltage differences, currents, current differences, impedances (voltages divided by currents) or impedance differences (e.g., (v1−v2)/(i1−i2) or (v1/ i1)−(v2/i2)). The system matrix 44 may be formed using any suitable process. Additionally, the signals may be real valued or complex valued (real and imaginary or amplitude and phase). Also, portions of the signals may be used (e.g., real only, imaginary only, amplitude only, or phase only) or in any combination. It also should be noted that the impedance signals predominantly contain information due to physical body deformation (e.g., movement of the patient).

With the system matrix 44 of one or more relationships defined, one or more techniques or methods are used to separate the signals to determine, for example, one or more underlying signals, which correspond to one or more physiological or non-physiological parameter of interest. The techniques or methods may include, but are not limited to, one or more of the following:

1. Principal component analysis;
2. Independent component analysis;
3. Other blind source separation techniques;
4. Template-based fitting, statistical templates or geometric templates;
5. Model-based fitting, statistical models or geometric models;
6. Spectral techniques across multiple relationships;
7. Choosing one or more pre-determined leads or lead sets based upon estimating the type of motion; and/or
8. Using a learning period during no motion to determine weights, templates, or models (either initially or periodically revisited).

Figure 3:
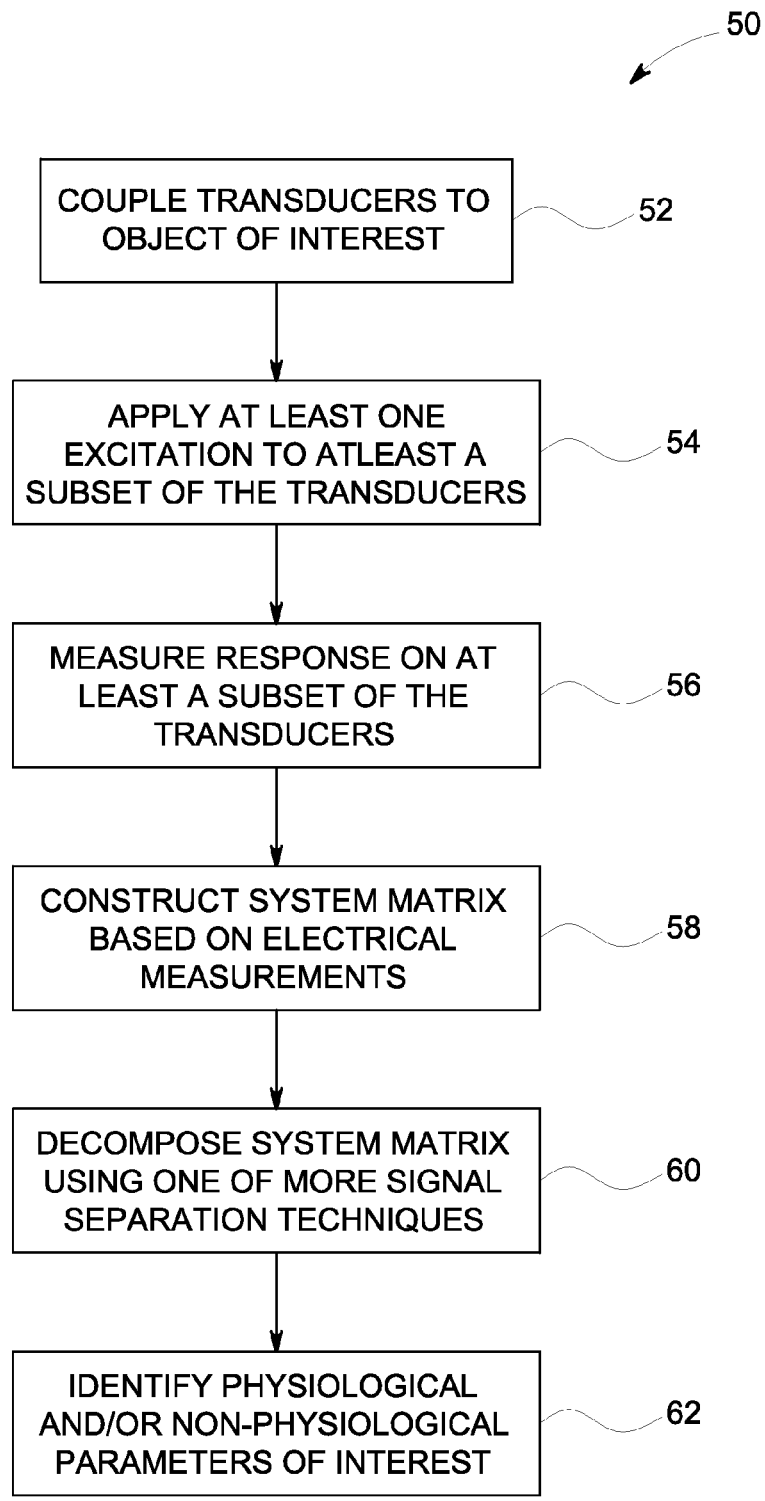
FIG. 3 is a flowchart of a method in accordance with various embodiments to extract physiological parameters from electrical measurements.

In accordance with various embodiments, a method 50 is performed to extract physiological parameters from electrical measurements as shown in FIG. 3. In particular, a plurality of transducers, for example in this embodiment a plurality of electrodes (e.g., eight electrodes), are coupled (e.g., applied) to an object of interest (e.g., a body or volume of interest) at 52. In some embodiments, such as when monitoring a patient, a plurality of electrodes may be applied to the skin of the thorax of the patient. As described herein, different configurations of electrode positioning may be provided, such as using standard ECG lead positioning.

Thereafter, in one exemplary embodiment, at least one excitation, for example, electrical currents are applied to at least a subset of the transducers, for example, one or more of the electrodes at 54. For example, a low level current, such as an EIS/EIT suitable current is applied to one or more of the electrodes. Thereafter, in this embodiment, a response, for example, electrical voltages are measured on at least a subset of the transducers, for example, one or more of the electrodes at 56. In some embodiments the electrical voltages are measured simultaneously or concurrently on all of the electrodes. The electrode measurements in these embodiments, when taken in the context of the applied excitations, correspond to a measured electrical conductivity of the patient, which can change, for example, during ventilation. For example, air entering and exiting the lungs can change the resistance to current through the patient.

A system matrix is then constructed at 58, which in some embodiments includes constructing a system matrix of electrical measurements measured at the one or more of the transducers. For example, the system matrix may be constructed of measured responses, impedances and/or impedance differences. In one embodiment, a system matrix is constructed of impedances and impedance differences based on the currents applied to the plurality of electrodes and measured voltages at the plurality of electrodes. The system matrix may then be any suitable array of numbers or values corresponding to the measured voltages. Thereafter, system matrix decomposition is performed at 60 using any suitable signal separation technique as described in more detail herein.

The separated signals then may be used to identify physiological or non-physiological parameters of interest at 62. For example, ventilation and ambulatory motion signals may be separated and identified such that a breathing or ventilation rate of a moving patient may be monitored.

Figure 4:
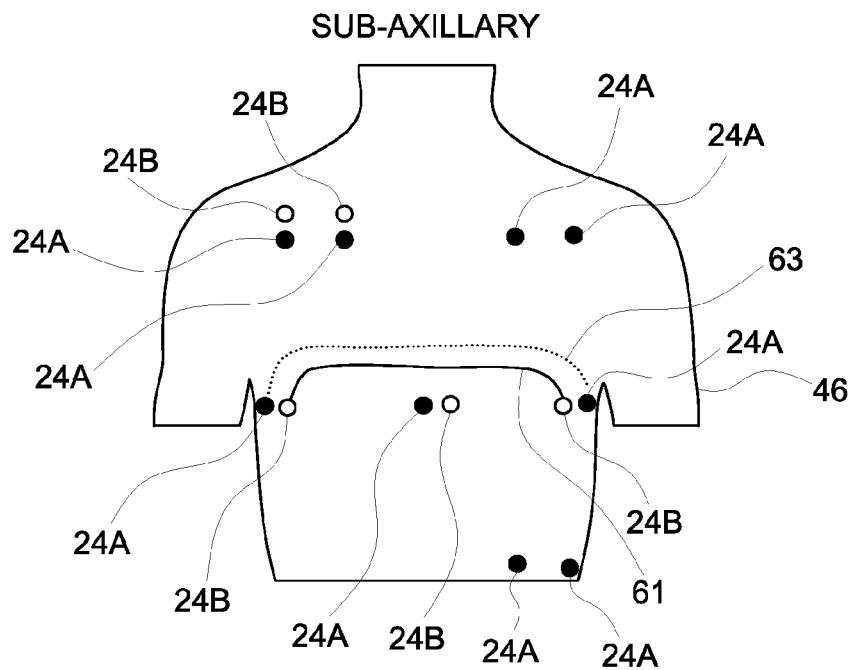
FIG. 4 is a diagram illustrating transducer placement in accordance with an embodiment.
Figure 5:
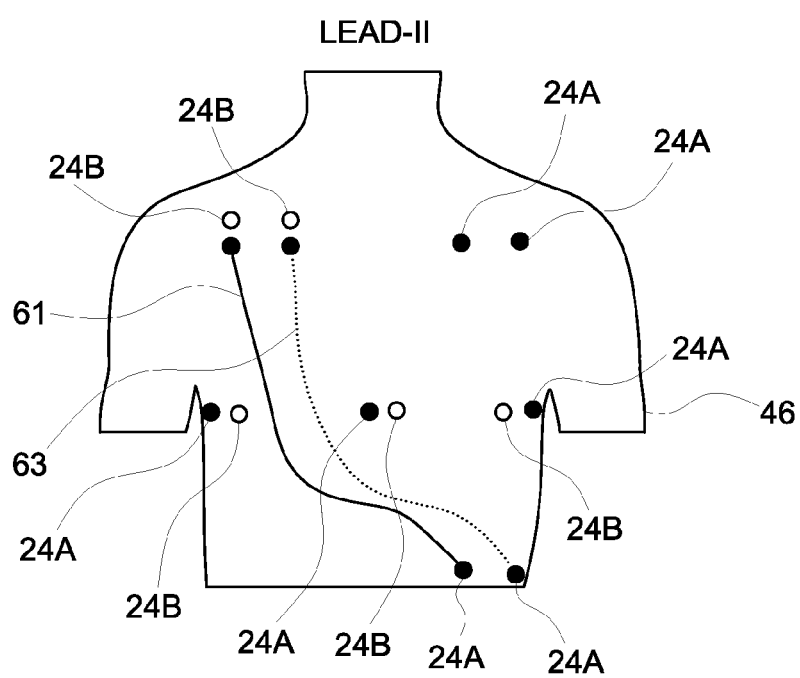
FIG. 5 is a diagram illustrating transducer placement in accordance with another embodiment.

As an example and in one embodiment, a set of eight electrodes are placed on the thorax with two electrodes nearby each other in each of the traditional ECG locations including the Right Arm, Left Arm, Right Leg, and Left Leg locations. However, different electrode configurations may be provided. For example, FIG. 4 illustrates a sub-axillary electrode placement configuration in accordance with one embodiment and FIG. 5 represents a Lead II electrode placement configuration, both on a human thorax 46. It should be noted that the front electrodes are identified by transducers 24*a* and the back electrodes are identified by transducers 24*b*. It also should be noted that the solid line represents an exemplary current path and the dashed line represents a corresponding exemplary measured voltage.

Figure 6:
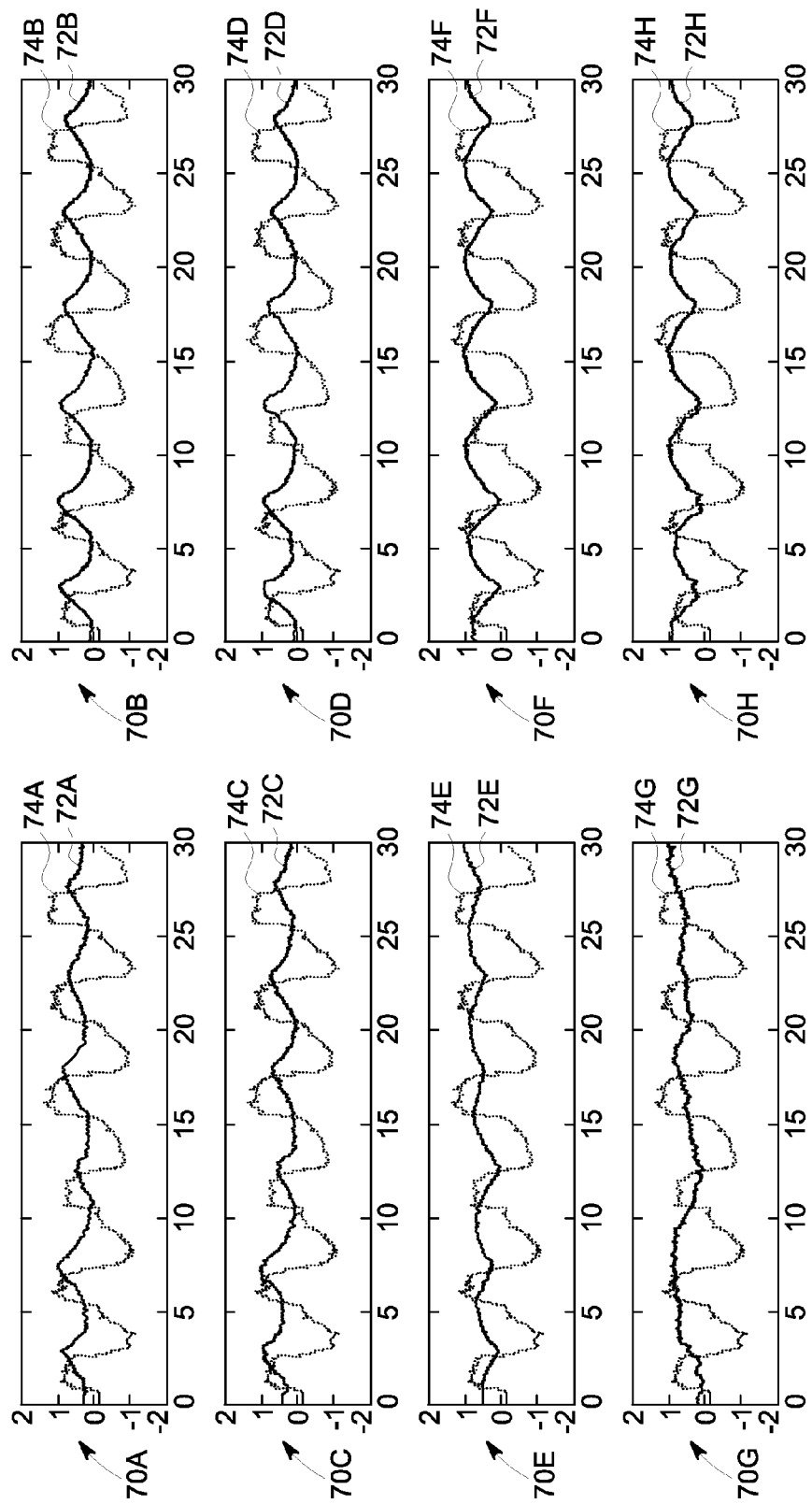
FIG. 6 are graphs illustrating data measurements in accordance with various embodiments.

In this illustrative embodiment, one transducer 24 of each pair of transducers 24 drives a small AC current (e.g., 60 μA) at a carrier frequency (e.g., 10 kHz) and the other transducer 24 of each pair does not drive current. The current path is represented by path 61. Thereafter, voltage measurements are performed for all transducers 24 including the current driving transducers 24 and the non-current driving transducers 24. The voltage measurement path is illustrated by path 63. The voltage measurements in various embodiments may be performed using a matched filter (at the carrier frequency) to provide an amplitude and phase or real and imaginary measurement. For example, the graphs 70*a*-70*g* in FIG. 6 represent the raw data measurements at the eight transducers 24 that are the input channels to the system matrix, where the horizontal axis represents time in seconds and the vertical axis represents arbitrarily scaled voltage amplitude. In the illustrated graphs 70*a*-70*g*, the impedance measurements are represented by the curves 72*a*-72*g* and ideal spirometer measurements are represented by the curves 74*a*-74*g*.

The various embodiments encompass many types of current excitation patterns. For example, in one embodiment, four current driving transducers 24 are driven with a 90 degree phase shift such that the sum of the driving currents is zero. An optional ground transducer 24 is placed on the thorax to return unbalanced currents. The ground transducer 24 may be placed anywhere on the body including, for example, the center of the chest, on a limb, or on the back. It also should be noted that different current patterns can be applied to set up electromagnetic fields in the body as described herein.

Figure 7:
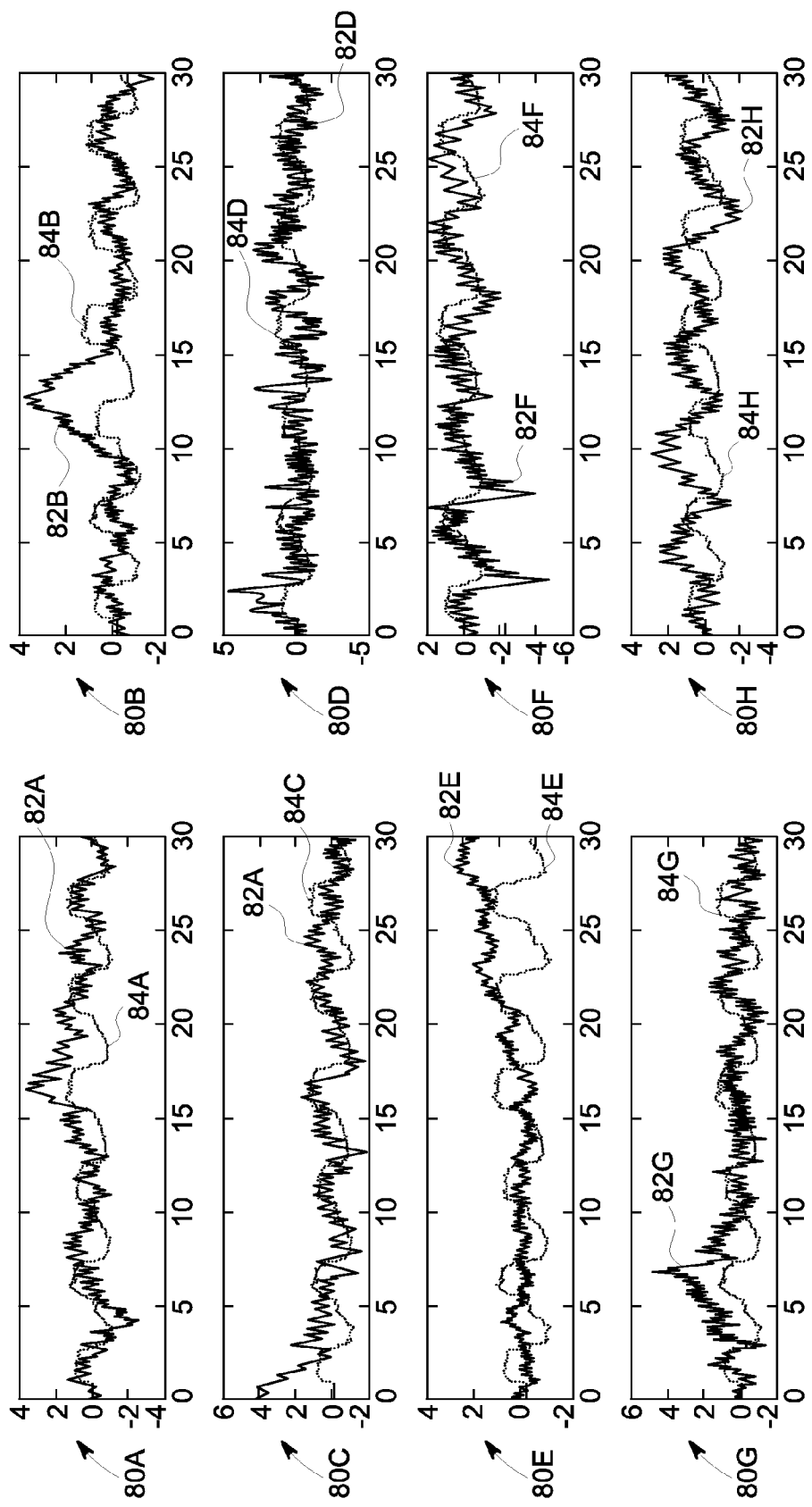
FIG. 7 are graphs illustrating separated signals in accordance with various embodiments.

The various embodiments then perform signal processing on the data or on a subset of the data. In this example, and in accordance with an illustrative embodiment, the signals are separated using a linear weighted sum of the multiplicity of impedance measurements, which signals are illustrated in the graphs 80*a*-80*g* of FIG. 7, corresponding to the same eight electrodes of FIG. 6. The separated signals, which correspond to elements of the decomposed system matrix, are represented by the curves 82*a*-82*g* and the ideal spirometer measurements are represented by the curves 84*a*-84*g*.

The coefficients for the weighted sum may be determined by using a least-squares minimization approach where the error to be minimized is the total sum of the squared error between the estimated signal and a reference signal. The reference signal used may be, for example, a measure of the flow or volume of air passed through the airway by use of a spirometer, which therefore shows separability of the signals using optimal coefficients. In one embodiment, the spirometer signal may be present during a learning phase to determine coefficients. In other embodiments, the spirometer signal is not present and blind separation techniques are used to estimate the optimal coefficients.

In various embodiments, one or more of the separated signals then may be identified and used to identify the value of the physiological parameter of interest, for example, ventilation separated from ambulatory motion and noise. In this example, the separate signal represented by the curve 82f may be used (from output channel 6) as a measure of, for example, patient breathing. Thus, in one or more of the eight curves 82a-82h, or a combination thereof, illustrated as waveforms over time, is contained the physiological signal of interest, for example, the breathing signal. In some embodiments, the determination of which measurements to use may be made based on apriori measurements or on-the-fly comparisons with an ideal spirometer waveform. In various embodiments, several breath cycles are used to determine the signal to use, which may include a voting process between electrodes measuring clean signals, such as signals having a positive peak on inhale and a negative peak on exhale. In general, a determination may be made as to which difference between electrode measurements has a periodic component where the motion is a transient process.

In other various embodiments, spectrum analysis may be performed to separate out the fundamental frequency component, and if such component is present across multiple electrodes, the signal is determined to be a good signal for use as the physiological measurement signal.

Figure 8:
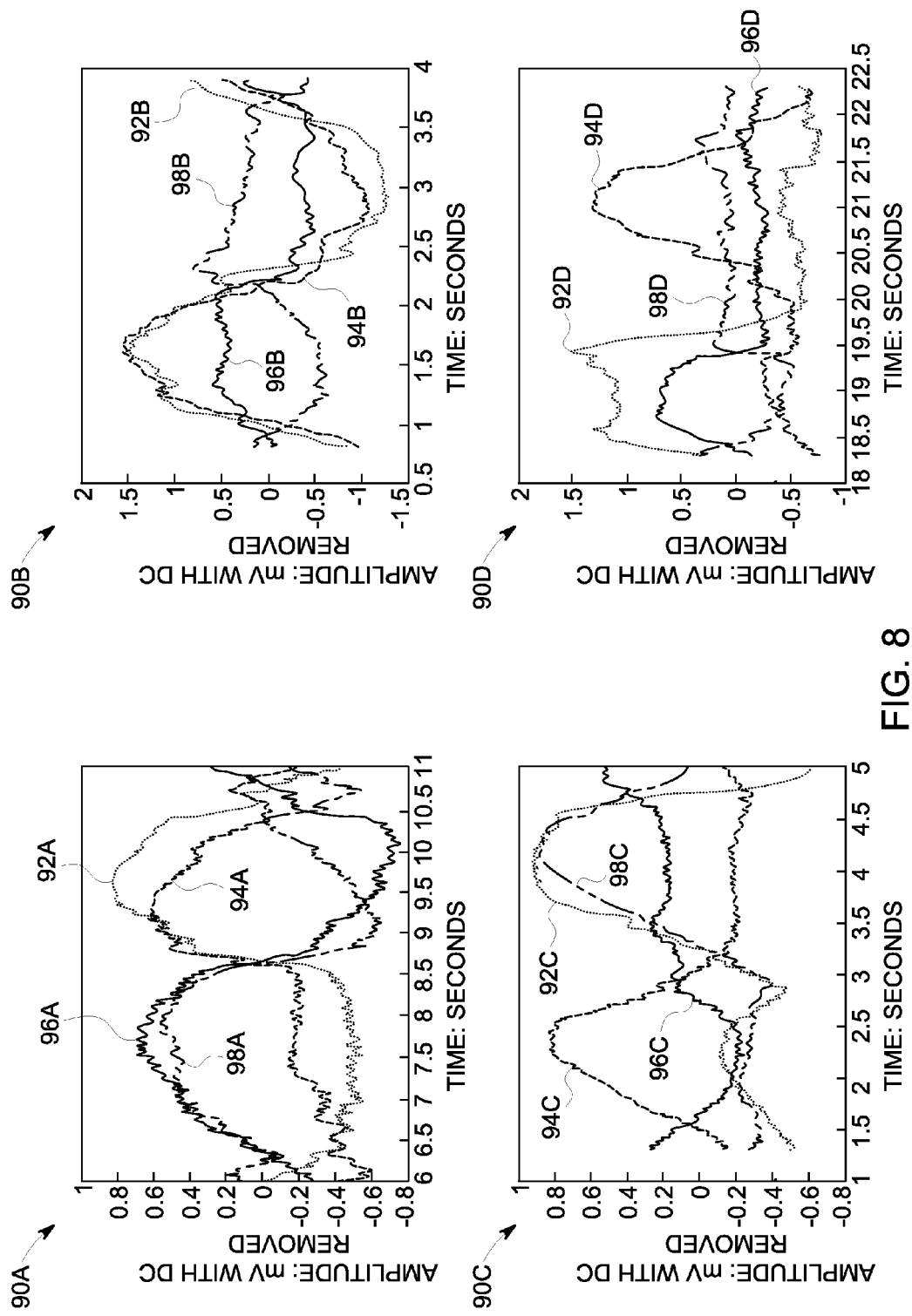
FIG. 8 are graphs illustrating waveforms corresponding to different ambulatory motions.

It should be noted that different motions may result in distinct measured differences as illustrated in graphs 90a-90d of FIG. 8. The signals 92, 94, 96 and 98 in graphs 90a-90d correspond to measurements of voltage on four different electrodes (illustrated as right arm, left arm, right leg and left leg measurements, respectively) in response to applied time-varying AC currents having a constant amplitude. In particular, graph 90a corresponds to a standing patient bending and holding his or her breath, graph 90b corresponds to a standing patient lifting both arms and holding his or her breath, graph 90c corresponds to a standing patient twisting and holding his or her breath and graph 90d corresponds to a standing patient alternating lifting of arms and holding his or her breath. Thus, the measured signals 92, 94, 96 and 98 correspond to measure ambulatory motion. It should be noted that bending forward or backwards changes the polarity of the signals.

Accordingly, in various embodiments, the signal separation process may include fitting the models to one or more of measured impedance patterns with a breath hold, which may be based on one or more previous measurements of different individuals. For example, the models may be based on studies of a group of patients and separated based on different factors, such as age, weight, and height.

Thus, various embodiments provide physiological parameter extraction from multiple electrical measurements from a plurality of transducers. For example, a signal separation process may be performed to identify breathing motion and ambulatory motion.

Additionally, although the various embodiments are described in connection with electrical (current and voltage) excitation, other sources of excitation may be provided. For example, magnetic, or radio-frequency (RF) excitations, among others, may be used in combination with the various embodiments. Thus, the measured responses are not limited to electrical responses, but may be, for example, magnetic or RF responses.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), field programmable gate arrays (FPGAs), graphical processing units (GPUs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for separating electrical measurement signals, the method comprising:
   obtaining electrical measurement signals acquired from a plurality of transducers coupled to a surface of an object, wherein the plurality of transducers deliver electrical current continuously or in modulation such that excitations are applied across a temporal frequency range to the surface of the object to generate surface potentials and an electromagnetic (EM) field within the object;
   constructing a system matrix to define one or more relationships between the electrical measurement signals; and
   decomposing the system matrix to separate the electrical measurement signals.

2. The method of claim 1, further comprising identifying at least one of physiological parameters or non-physiological parameters using the separated electrical measurement signals.

3. The method of claim 2, wherein the physiological parameters comprise at least one of ventilatory motion, cardiac motion and ambulatory motion.

4. The method of claim 2, wherein the non-physiological parameters comprise noise.

5. The method of claim 1, further comprising positioning the plurality of transducers on a surface of the object in an electrocardiography (ECG) electrode placement configuration.

6. The method of claim 1, further comprising applying an electrical excitation to at least one of the plurality of transducers, alone or in combination with a magnetic or radio-frequency excitation.

7. The method of claim 1, wherein obtaining electrical measurement signals comprises measuring at least one of an electrical voltage, current, magnetic response or radio-frequency response on all or a subset of the plurality of transducers.

8. The method of claim 1, wherein decomposing the system matrix comprises at least one of a principal component analysis, an independent component analysis, a blind source separation technique, a template-based fitting technique, a statistical template-based technique, a geometric template-based technique, a model-based fitting technique, a statistical model-based technique, a geometric model-based technique or a spectral analysis technique across more than one relationship.

9. The method of claim 1, wherein the one or more relationships comprise a relationship between electrical signals including at least one of voltages, voltage differences, currents, current differences, impedances, impedance differences, admittances, or admittance differences, wherein the one or more relationships may be real valued, imaginary valued or complex valued.

10. The method of claim 1, wherein the object is a person and the matrix is constructed for impedance measurements over time across multiple ventilation cycles of the person.

11. An impedance measurement system comprising:
    a plurality of transducers configured for positioning at a surface of an object, wherein the plurality of transducers correspond to a plurality of channels;
    an excitation driver electrically coupled to at least a subset of the plurality of channels and configured to generate electrical excitations on at least a subset of the plurality of transducers;
    a response detector configured to measure a response on at least a subset of the plurality of transducers to define electrical measurement signals; and
    a processor having a physiological parameter extraction module configured to construct a system matrix to define one or more relationships between the electrical measurement signals and decompose the system matrix to separate the electrical measurement signals;
wherein the plurality of transducers deliver electrical current continuously or in modulation such that excitations are applied across a temporal frequency range to the surface of the object to generate surface potentials and an electromagnetic (EM) field within the object.

12. The impedance measurement system of claim 11, wherein the physiological parameter extraction module is further configured to identify at least one of physiological parameters and non-physiological parameters using the separated electrical measurement signals.

13. The impedance measurement system of claim 11, wherein the plurality of transducers comprise electrodes coupled to skin of a patient in an electrocardiography (ECG) electrode placement configuration.

14. The impedance measurement system of claim 11, wherein the plurality of transducers comprise electrodes coupled to skin of a patient in a non-electrocardiography (ECG) electrode placement configuration.

15. The impedance measurement system of claim 11, wherein the plurality of transducers comprise one of electrical, magnetic or radio-frequency transducers.

16. The impedance measurement system of claim 11, wherein the electrical excitations comprise one of current, voltage, magnetic or radio-frequency excitations.

17. The impedance measurement system of claim 11, wherein the electrical measurement signals comprises at least one of current, voltage, magnetic and radio-frequency signals.

* * * * *